US012653701B2

(12) United States Patent
Eder

(10) Patent No.: US 12,653,701 B2
(45) Date of Patent: Jun. 16, 2026

(54) HYDRAULIC ACTUATOR FOR ORTHOTICS OR PROSTHETICS AND ORTHOPAEDIC ARRANGEMENT

(71) Applicant: OTTO BOCK HEALTHCARE PRODUCTS GMBH, Vienna (AT)

(72) Inventor: Florian Eder, Vienna (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 710 days.

(21) Appl. No.: 17/641,805

(22) PCT Filed: Aug. 31, 2020

(86) PCT No.: PCT/EP2020/074220
§ 371 (c)(1),
(2) Date: Mar. 9, 2022

(87) PCT Pub. No.: WO2021/047934
PCT Pub. Date: Mar. 18, 2021

(65) Prior Publication Data
US 2022/0370213 A1     Nov. 24, 2022

(30) Foreign Application Priority Data

Sep. 12, 2019     (DE) ...................... 10 2019 124 545.1

(51) Int. Cl.
*A61F 2/74* (2006.01)
*A61F 2/60* (2006.01)
(52) U.S. Cl.
CPC .............. *A61F 2/742* (2021.08); *A61F 2/604* (2013.01)
(58) Field of Classification Search
None
See application file for complete search history.

(56) References Cited

U.S. PATENT DOCUMENTS

| 5,062,857 A | 11/1991 | Berringer et al. |
| 7,963,998 B2 | 6/2011 | Boiten |
| | (Continued) | |

FOREIGN PATENT DOCUMENTS

| CN | 101389291 A | 3/2009 |
| CN | 102164571 A | 8/2011 |
| | (Continued) | |

OTHER PUBLICATIONS

International Search Report and Written Opinion issued in PCT/EP2020/074220, Mar. 18, 2021, 13 pgs.

(Continued)

*Primary Examiner* — Bruce E Snow
(74) *Attorney, Agent, or Firm* — HOLLAND & HART LLP

(57)     ABSTRACT

A hydraulic actuator for orthotics or prosthetics, comprising a control element with a housing, in which a cylinder is arranged, in which a piston is mounted so as to be movable and divides the cylinder into a flexion chamber and an extension chamber, a fluidic connection is arranged between the flexion chamber and the extension chamber, and in each of said chambers there is arranged a control valve for influencing the extension movement or flexion movement, a motorised pump being arranged in the fluidic connection, with the hydraulic fluid being conducted from one chamber to the pump through at least one control valve in an intake-side connection line, and a check valve being arranged in a delivery-side connection line from the pump to the other chamber and blocking a return flow of the pumped medium from this chamber to the pump against the conveying direction of the pump.

19 Claims, 4 Drawing Sheets

(56)                         References Cited

U.S. PATENT DOCUMENTS

| | | | |
|---|---|---|---|
| 10,406,001 | B2 | 9/2019 | Harris et al. |
| 11,408,444 | B2 | 8/2022 | Mejia Nino et al. |
| 2011/0166489 | A1 | 7/2011 | Angold et al. |
| 2013/0150980 | A1* | 6/2013 | Swift ........................ A61F 2/70 |
| | | | 623/24 |
| 2015/0164660 | A1 | 6/2015 | Will et al. |
| 2015/0202057 | A1 | 7/2015 | Zahedi et al. |
| 2015/0320573 | A1 | 11/2015 | Gramnaes |
| 2018/0098864 | A1 | 4/2018 | Auberger et al. |

FOREIGN PATENT DOCUMENTS

| | | | |
|---|---|---|---|
| CN | 104602650 | A | 5/2015 |
| CN | 108210254 | A | 6/2018 |
| GB | 2537900 | A | 11/2016 |
| GB | 2566310 | A | 3/2019 |
| JP | S58-22054 | A | 2/1983 |
| JP | S59-71747 | A | 4/1984 |
| WO | 2010/005473 | A1 | 1/2010 |
| WO | 2018065570 | A1 | 4/2018 |
| WO | 2018/161023 | A1 | 9/2018 |
| WO | 2019/162331 | A1 | 8/2019 |

OTHER PUBLICATIONS

Japan Patent Office "Office Action", issued in connection with Japan Patent Application No. 2022-510849. dated Apr. 23, 2024 (8 pages) (4 pages of English Translation and 4 pages Original Document).

* cited by examiner

HYDRAULIC ACTUATOR FOR ORTHOTICS OR PROSTHETICS AND ORTHOPAEDIC ARRANGEMENT

CROSS REFERENCE TO RELATED APPLICATIONS

This is a national phase application of International Application No. PCT/EP2020/074220, filed 31 Aug. 2020, which claims the benefit of German Patent Application No. 10 2019 124 545.1, filed 12 Sep. 2019, the disclosures of which are incorporated herein, in their entireties, by this reference.

TECHNICAL FIELD

The invention relates to a hydraulic actuator for orthoses or prostheses, comprising a control element with a housing in which a cylinder is arranged, in which a piston is mounted movably and divides the cylinder into a flexion chamber and an extension chamber, wherein a fluidic connection is arranged between the flexion chamber and the extension chamber, in which fluidic connection a control valve is arranged for influencing the extension movement and flexion movement respectively, and wherein a motor-driven pump is arranged in the fluidic connection. The invention also relates to an orthopedic device, in particular an orthosis or prosthesis having such a hydraulic actuator.

BACKGROUND

Orthoses or prostheses often have joint devices which have an upper part and a lower part that are mounted on each other so as to be pivotable about at least one pivot axis. In orthoses, the joints are usually arranged next to the natural joints, for example next to the ankle joint, the knee joint and/or the hip joint. Likewise, orthoses for the upper extremities or the trunk can be equipped with appropriate joint devices. Prostheses replace limbs that are not present or that are no longer present. The joints used in prostheses replace the respective natural joints. To be able to influence the movement of the upper part relative to the lower part, purely passive resistance devices and/or dampers are provided from the prior art. The resistance behavior of these devices can be permanently set; alternatively, sensors are arranged on the prosthesis or orthosis or on the respective limb and determine sensor values on the basis of which the resistance device or the damper is controlled. In a hydraulic damper, valves are opened or closed or cross sections of flow are changed in order to change flow resistances. In other resistance devices, magnetorheological properties can be changed, brakes activated or motors switched to generator mode. The change in resistances can be made for the extension movement and/or the flexion movement. This is then what is called a mechatronic system.

The change in the resistances by the damper or the resistance device can be supplemented by a drive, such that a purely passive resistance device becomes an actuator which, in addition to providing different resistances or damping properties, alternately causes or at least supports an extension and/or flexion. Hydraulic systems are usually provided for this purpose, since purely pneumatic systems cannot be operated with the necessary precision, because the fluid used in a pneumatic system is compressible.

WO 2010/005473 A1 discloses an orthopedic device in the form of a prosthesis or orthosis and a method for controlling same, in which a motor-driven pump pumps hydraulic fluid into a flexion chamber or into an extension chamber. The pump can be switched to a passive operation in which the motor is not driven, with the result that a hydraulic damper is created. The hydraulic resistance is then set using control valves, check valves and switching valves. Disadvantages of such a design are the required active valves and the fact that a switching valve has to be opened before the pump can initiate or support an active movement. A further disadvantage is that there is no low-pressure region that could absorb a pump leakage.

SUMMARY

The object of the present invention is to make available a hydraulic actuator and an orthopedic device with which a disturbance-free transition from a passive to an active operation is possible with minimal control complexity.

This object is achieved by a hydraulic actuator having the features of the main claim and by an orthopedic device having the features of the additional independent claim. Advantageous embodiments and developments of the invention are disclosed in the subclaims, the description and the figures.

In the hydraulic actuator for orthoses or prostheses, comprising a control element with a housing in which a cylinder is arranged, in which a piston is mounted movably and divides the cylinder into a flexion chamber and an extension chamber, wherein a fluidic connection is arranged between the flexion chamber and the extension chamber, in which fluidic connection a control valve is arranged for influencing the extension movement and flexion movement respectively, and wherein a motor-driven pump is arranged in the fluidic connection, provision is made that on the suction side the hydraulic fluid is conveyed from one chamber to the pump through at least one control valve in a connection line, and on the pressure side a check valve is arranged in a connection line from the pump to the other chamber, and the check valve blocks a backflow of the pumped medium from this chamber to the pump counter to the delivery direction of the pump. With such a hydraulic actuator, it is possible to simply switch from a purely passive operation, in which hydraulic fluid is conveyed through a corresponding control valve and if appropriate a check valve through the connection line from the extension chamber to the flexion chamber or vice versa from the flexion chamber to the extension chamber, to an active operation simply by switching on the pump, without a further valve having to be actively switched. By starting up the pump and feeding the hydraulic fluid under pressure in the direction of the corresponding chamber, the actuator becomes an active actuator in the sense that the pump delivers pressure fluid against the check valve. With a corresponding pressure difference, when the pressure from the pump is greater than the pressure against it, the check valve is opened and the pump couples in the hydraulic system. This coupling in takes place without active switching of the check valves, which means that synchronization of the start-up of a pump and of the opening of a switching valve is superfluous. This leads to gentle coupling of the pump into the hydraulic system of the actuator, without additional manipulation of the existing hydraulic valves, for example of the control valves, being necessary for influencing the extension damping and/or flexion damping. It is additionally possible that, upon a transition from a passive operating mode to an active operating mode, the pump can run up to speed in advance, for example in order to dampen a movement that has already been initiated and to counteract it. Flexion can thus be counteracted by starting the pump in the extension direction, for example also in connection with a change in the flexion resistance by changing the setting of a control valve. If the valve for influencing the flexion movement is located in a closed state, the extension movement and reversal of movement can already be initiated at the joint. A movement reversal at the joint then occurs automatically as soon as the pump pressure exceeds the pressure on the piston within the cylinder.

The design of the hydraulic actuator is particularly advantageous when only one check valve is arranged between the pump and the chamber pressurized by the pump and when the hydraulic fluid is conveyed by the pump only through a correspondingly directed check valve and the respective connection line to the desired chamber. Further control valves are no longer provided in the pressure-side connection line from the pump to the respective chamber, which results in a simplified set-up of the hydraulic actuator and a reduction in the control complexity.

The respective pressure-side connection line, with which the pump is connected to the fluidic connection, can open out between two check valves which are oriented in the same direction and arranged in series, as a result of which it is possible, in addition to a purely passive mode of operation of the hydraulic actuator, to simply change to active operation with little circuitry outlay, namely by activating the pump.

In a variant of the invention, provision is made that a check valve blocks a connection between the pressure-side connection line and a suction-side connection line. Particularly in the case of an actuator in which a movement is intended to be supported by a pump in only one direction of movement, such an arrangement saves space and cuts down on material. Instead of as in the case of line routing in which the pressure-side connection line is arranged between two check valves oriented in the same direction, this makes it possible to block a suction-side connection line or a low-pressure connection line between the extension chamber and the flexion chamber by a check valve switched in parallel. The two check valves are oriented in the same direction, such that hydraulic fluid that flows from the pump passes through the pump-side check valve, but cannot open the check valve that separates the high-pressure side from the low-pressure side. By virtue of this circuit arrangement, it is moreover possible to operate the actuator passively in both directions and at the same time to implement an active mode of operation in only one direction. In this way, one check valve can be saved by comparison with an operating mode that is active and passive in both operating directions.

In the fluidic connection between the flexion chamber and the extension chamber, a central line can be formed into which outflow lines from the flexion chamber and the extension chamber open. Supply lines lead from the central line to suction-side inlets or to at least one suction-side inlet of the pump. If the actuator is designed to be active in both directions and can actively support both the extension movement and the flexion movement, a plurality of inlets can be present. Alternatively, an outlet in one delivery direction can represent the inlet in the other delivery direction. The hydraulic circuit diagram is then set up symmetrically, which makes it possible, via the direction of rotation of the pump motor, to change the delivery direction and thus also to specify the direction of movement of the actuator or the joint. A prerequisite for this is that the pump can deliver in both directions, which is the case, for example, with an internal gear pump, an external gear pump or a toothed ring pump. All other types of pumps which can deliver in both directions and whose delivery direction is dictated by the direction of rotation can likewise be used. The outflow lines preferably lead through the respective control valve into the central line. Depending on the direction of flow, an outflow line can at the same time form a pressure-side connection line.

In a further development of the invention, provision is made that the pump has two pressure connections which are each connected to the fluidic connection via a respective connection line. Both connection lines open out between two check valves which are designed as pairs of check valves and which act in the same direction and are arranged in series, wherein the pairs of check valves have oppositely directed flow directions. With this symmetrical circuit set-up, it is possible to make available a hydraulic actuator with only two control valves and four passive check valves, which hydraulic actuator can be operated passively and actively both in the flexion direction and in the extension direction. As soon as the pump is not active, i.e. is not driven by a motor, the hydraulic system is automatically switched to a passive mode, with the respective hydraulic resistances being influenced only via the two control valves. A leakage and a pressure loss in the pump are ruled out by the particular arrangement of the check valves, as a result of which the leaktightness requirements to be met by the pump are moderate. The leaktightness of the hydraulic cylinder is ensured by the particular circuitry of the check valves such that, even if the hydraulic cylinder is blocked by closed valves, the piston does not sink due to leakage through the pump.

In a further development of the invention, provision is made that the central line leads to return lines to the extension chamber and the extension chamber, and in the respective return line a check valve is arranged which prevents a backflow into the central line. The return lines branch off from the central line, with a branch leading to the suction-side inlet of the pump only in one direction of movement during active operation. In an embodiment for active operation in both directions of movement, a branch to the respective suction-side inlet is provided, the two branches being arranged on the other side of two oppositely directed check valves. Thus, a connection line leads to a return line to the extension chamber or the flexion chamber.

In a further development of the invention, provision is made that a compensation volume is connected to the fluidic connection, in particular connected to a central line which allows liquid to be fed into the flow circuit between two control valves. A compensation volume is particularly advantageous if only one piston rod protrudes from a hydraulic cylinder, such that the hydraulic actuator is generally secured to the orthosis or prosthesis or orthopedic device with one end via the housing and with another end via a piston rod. The compensation volume compensates for the volume differences between the extension chamber and the flexion chamber caused by the retracting or extending piston rod. The piston is preferably coupled to the piston rod, which in turn protrudes from the housing of the cylinder and is linearly movable.

The pump is designed or connected so as to be able to be operated to fill both the extension chamber and the flexion chamber. If the pump cannot be switched via the direction of rotation, a switching valve can be arranged in the fluidic connection, which however would increase the control complexity.

The check valves are advantageously designed as passive valves, for example spring-loaded ball valves or flap valves.

The control valves are advantageously controlled electronically. For this purpose, sensors can be arranged on the orthopedic device, e.g. orthosis or prosthesis, or on the patient, which sensors detect state variables via the orthopedic device or the respective movement state and transmit these to a controller that is equipped with a data processing device, for example a processor. Evaluation programs can be stored in the processor in order to evaluate the raw sensor data or in order to operate actuators on the basis of the sensor values so as to open or close the control valves. The control valves can reduce or enlarge the cross section of flow and, if necessary, close it completely in order to block the fluidic connection between the extension chamber and the flexion chamber. Through a reduction in the cross section of flow, the flow resistance is increased and a corresponding movement is made more difficult; if it is blocked, a movement is suppressed. If both control valves are completely closed, the actuator is blocked. When the actuator is arranged on a joint, a movement of the joint about a pivot axis is thus blocked.

In a further development of the invention, provision is made that a plurality of control elements are fluidically coupled to the pump. In particular, the mechanical components with the cylinder, the piston rod protruding therefrom and the valves, possibly with compensation volume, are seen as the control element. The control element can be designed with a separate housing, which is separate from the housing of the pump and is coupled to the pump via hydraulic lines. This makes it possible to provide a modular structure and to couple an individual pump to several control elements. It is thus possible to hydraulically couple an individual pump to, for example, two control elements, such that each control element can be assigned to a different joint. A first control element can be used, for example, as an actuator and resistance device for an orthotic knee joint or prosthetic knee joint, while the second control element, likewise coupled to the pump, can be used as an actuator for an orthotic ankle joint or prosthetic ankle joint.

The invention also relates to an orthopedic device with a hydraulic actuator as has been described above. The orthopedic device is designed in particular as an orthosis or prosthesis, while the actuator is designed and suitable in particular as a resistance device and drive for a joint within the orthopedic device.

The hydraulic actuator is designed to be operable as an active actuator or as a passive actuator and, by virtue of the hydraulic coupling on the pressure side via a check valve, does not require any mechatronic control for switching between a passive mode of operation and an active mode of operation.

The control element can be arranged between a joint device with an upper part and a lower part attached to the latter in an articulated manner. In a further development of the invention, provision is made that two control elements connected to a common pump are arranged on different joint devices of the orthopedic device.

BRIEF DESCRIPTION OF THE DRAWINGS

Illustrative embodiments of the invention are explained in more detail below with reference to the accompanying figures, in which.

DETAILED DESCRIPTION

Figure 1:
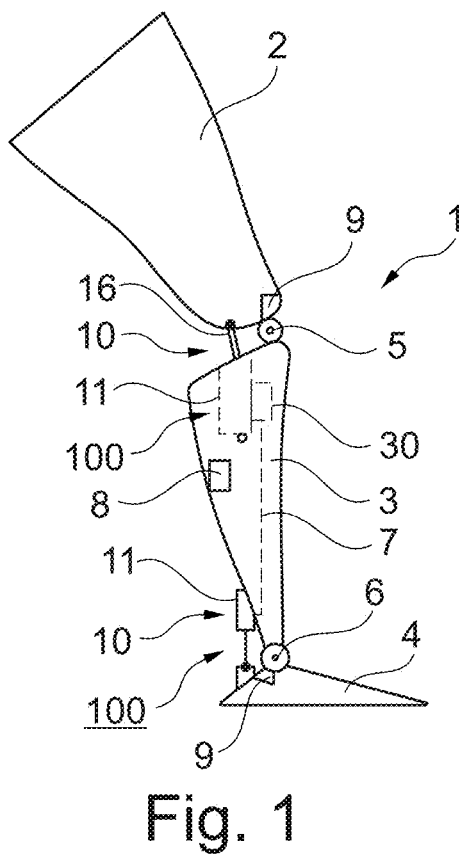
FIG. 1 shows a schematic representation of a prosthesis with hydraulic actuator.

FIG. 1 is a schematic representation of an orthopedic device 1 in the form of a prosthesis. The orthopedic device 1 has an upper part 2 in the form of a prosthesis socket, which is pivotably connected to a lower part 3 via a first joint device 5. A prosthetic foot 4 is pivotably mounted on the distal end of the lower part 3 via a second joint device 6. Instead of the embodiment of the orthopedic device 1 as a prosthesis, which replaces a leg that is not present or that is no longer present, the orthopedic device 1 can also be designed as an orthosis. Instead of a thigh socket 2, in which a thigh stump is received in order to fit the prosthesis on the patient, the upper part 2 can be designed as a thigh rail or thigh shell that is applied to the patient's thigh. The lower part 3 is then designed as a lower-leg rail or lower-leg shell, which is secured to the lower leg of the patient, for example by straps, belts or hook-and-loop fasteners. At the distal end of the lower part 3, instead of a prosthetic foot 4, a footrest can be pivotably attached to the lower part 3 via the second joint device 6. In principle, it is also possible that, instead of two joint devices 5, 6, the orthopedic device spans only one joint and, for example as a lower-leg prosthesis, is designed as a lower-leg socket for accommodating a lower-leg stump. A prosthetic foot can then be secured in an articulated manner to the lower-leg socket; alternatively, an orthosis can span only the ankle joint or only the knee joint, and the respective joint device is then arranged at the level of the respective natural joint. Furthermore, the orthopedic device can also be arranged on upper extremities, for example as an orthosis that is placed on an arm or as a prosthesis that replaces an arm or part of an arm. The orthopedic device can likewise be designed to rest on the trunk of a user. In an embodiment of the orthopedic device 1 with a plurality of joint devices 5, 6, a lower part for a first joint device 5 can form an upper part for a second joint device 6. An upper part is then the component that is arranged proximally with respect to the joint device, and a lower part is the component that is arranged distally with respect to the joint device.

In the illustrative embodiment shown in FIG. 1, a hydraulic actuator 100 is arranged in the lower part 3, which is designed as a lower-leg part, which hydraulic actuator 100 has a control element 10 with a motor-driven pump 30 arranged thereon. The hydraulic actuator 100 has a housing 11 which is fastened to the lower part 3. The fastening can be made pivotable in order to compensate for relative movements between the housing 11 and the lower part 3 during use. A piston rod 16, which is secured to the upper part 2, protrudes from the housing 11 of the control element 10. Within the hydraulic actuator 100, which will be explained in more detail later, a cylinder is arranged with a hydraulic piston mounted displaceably therein, which hydraulic piston can be actively displaced via the pump 30. As a result of the displacement of the piston, the piston rod 16 is also displaced, which leads to an extension or flexion of the upper part 2 relative to the lower part 3 about the pivot axis of the joint device 5. The pump 30 can be integrated in the housing 11 of the hydraulic actuator 100 or can be equipped with a separate housing and coupled to the hydraulic actuator 100 via lines.

In the illustrative embodiment according to FIG. 1, a second hydraulic actuator 100 is arranged in the region of the ankle joint, is designed with a control element 10 and is coupled via a hydraulic line 7 to the pump 30 of the hydraulic actuator 100 arranged in the region of the knee joint. When the pump 30 is activated, hydraulic fluid can be applied either to the knee-side hydraulic actuator 100 or to the ankle-side hydraulic actuator 100. In principle, it is also possible for both hydraulic actuators 100 to be simultaneously provided with hydraulic fluid from the pump 30.

Both hydraulic actuators 100 can be operated in an active mode, in which the pump 30 is driven, or in a passive mode, wherein the hydraulic actuator 100 operates as a resistance device, in particular as a hydraulic damper, in the passive mode. Sensors 9 can be arranged on orthopedic device 1, for example force sensors, torque sensors, angle sensors, position sensors, acceleration sensors, gyroscopes and/or inertial measurement units (IMU), which are connected to a controller 8 by wires or wirelessly. Processors or other data processing devices can be accommodated in the controller 8, and the energy supply is provided via a battery or an accumulator. The controller 8 processes the sensor values and sets control valves within the hydraulic actuator 100 in order to adapt the flow resistance in the extension direction and/or flexion direction to the respective load and/or gait situation. In principle, it is also possible for the respective control valve to be set once and adapted to the respective user.

Figure 2:
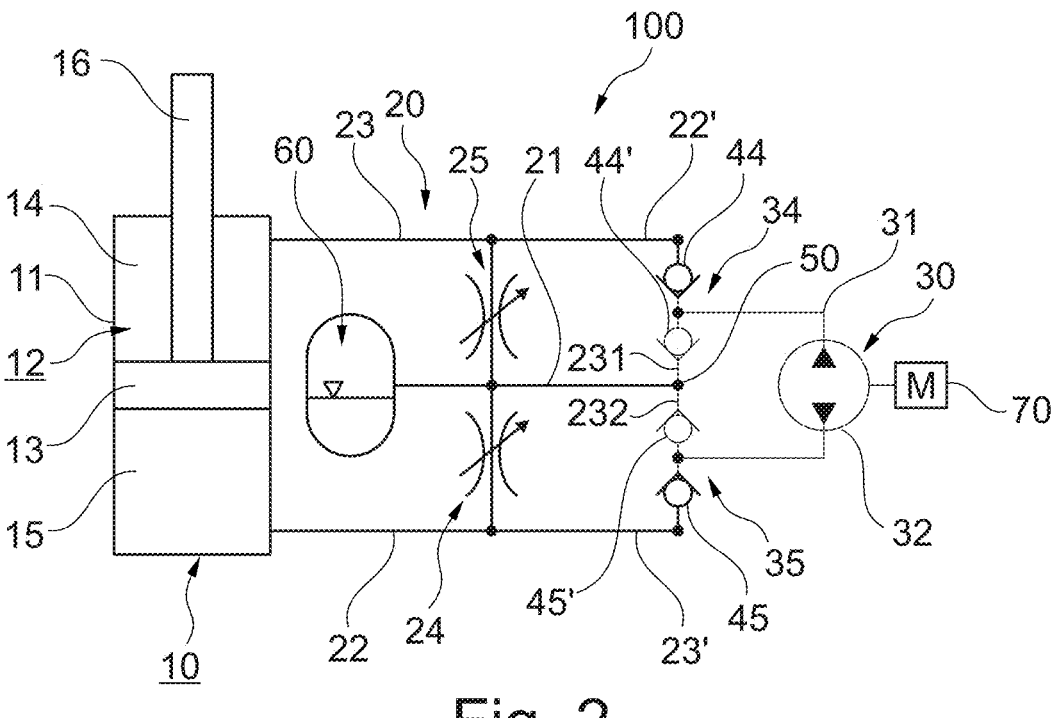
FIG. 2 shows a first hydraulic circuit diagram for an active operating mode in two directions.

FIG. 2 shows a hydraulic circuit diagram of the hydraulic actuator 100. A control element 10 has a housing 11 with a cylinder 12 formed therein. A hydraulic piston 13 is arranged in a longitudinally displaceable manner within the cylinder 12 and divides the cylinder 12 into a flexion chamber 15 and an extension chamber 14. A piston rod 16 is attached to the piston 13, protrudes from the housing 11 and is coupled to a component of the orthopedic device 1, for example the upper part 2. The other component of the orthopedic device 1 is coupled to the housing 11. During a flexion movement, the piston rod 16 is moved into the housing 11 and the volume of the flexion chamber 15 is reduced. At the same time, the volume of the extension chamber 14 is increased; on account of the volume of the piston rod 16 there is a volume difference between the two chambers 14, 15 during a displacement. The two chambers 14, 15 are coupled to each other via a fluidic connection 20, such that hydraulic fluid can flow from the flexion chamber 15 into the extension chamber 14 and vice versa. In order to compensate for the difference in volume change caused by the piston rod 16, a compensation volume 60 is arranged in the fluidic connection 20, into and out of which compensation volume 60 hydraulic fluid can be conveyed into the respective chamber 14, 15.

In the arrangement according to FIG. 2, the fluidic connection 20 has connection lines 22, 23 which branch off from or lead to the respective chamber 14, 15. Furthermore, two control valves 24, 25 are arranged in the fluidic connection 20, through which valves 24, 25 hydraulic fluid is conveyed. The control valves 24, 25 lead via a connection line to a central line 21, into which a line from the compensation volume 60 also opens. In the illustrative embodiment shown in FIG. 2, the control valve 24 is the flexion control valve and the control valve 25 is the extension control valve. Parallel to the connection line, parallel supply lines 231, 232 are arranged in which check valves 44, 44', 45, 45' are arranged. In the respective supply lines 231, 232, the check valves are arranged as check valve pairs 44, 44' and 45, 45', wherein the check valve pairs are oriented in the same direction, such that the fluid from the central line 21 can only flow through the check valves 44, 44', 45, 45', but cannot flow back. Between each of the check valve pairs 44, 44' and 45, 45', a connection line 34, 35 is arranged which leads to an inlet or outlet 31, 32 of the pump 30. Depending on the drive direction or the delivery direction of the pump 30, the connection lines 22, 23, 34, 35 become suction-side or pressure-side connection lines, and similarly an inlet can become an outlet, and vice versa. From the check valve pairs 44, 44' and 45, 45', return lines 22', 23' run to the respective chambers 14, 15, wherein the return lines 22', 23' can open into connection lines 23, 22. Within these lines, which lead from a check valve 44, 45 to the respective chamber 14, 15, preferably no further fluidic influence is provided, in particular no valve or throttle. The control element 10 can receive the pump 30 in an integrated manner; the valves can likewise be arranged within the housing 11 or on the housing 11, in order to achieve the most compact construction possible of the hydraulic actuator 100.

By blocking the supply lines 231, 232 in opposite directions in terms of flow, a connection 50 is blocked between the respective pressure-side connection line 34, 35, which leads from the check valve 44', 45' to the pump 30, and a suction-side connection line 22, 23, through which hydraulic fluid is delivered from the low-pressure region to the pump 30. The circuit arrangement according to FIG. 2 makes it possible to operate the hydraulic actuator 100, by virtue of its symmetrical set-up, in both operating directions, both in terms of flexion and extension. It is also possible to configure the pump 30 to be deactivated and removed from the flow circuit to the extent that, during passive operation of the hydraulic actuator 100, no pressurized hydraulic fluid is present at the pump inlet. This prevents a situation in which, when the control valves are blocked, the piston 13 sinks due to sealing problems or due to design-related leakage in the pump 30. Only by reversing the direction of rotation of the pump 30, for example by changing the direction of rotation of the motor 70 connected to the pump 30, is it possible to switch from an active extension operation to an active flexion operation.

By arranging the pump connection lines 34, 35 within a check valve cascade, it is possible, in an active operating mode, to couple the pump 30 into the system without adjustment of control valves. Pressurized hydraulic fluid is conveyed from an outlet of the pump 30 through a passive check valve to the respective chamber of the hydraulic cylinder 12. An additional valve actuation for coupling in the pressure fluid is no longer necessary, as a result of which the control complexity is reduced and installation space is saved. The corresponding check valve 44, 45 opens only when the pressure from the pump 30 is greater than the closing pressure of the check valve 44, 45. Dispensing with a valve actuation also avoids a jerky system behavior, which occurs when the time point of the same pressure on both valve sides for opening the valve in the case of a control valve is not exactly reached. In addition, it is possible that, upon transition from a passive operating mode to an active operating mode, the pump 30 can be activated in advance in order to brake a movement of the control element 10 in the opposite direction. Advantageously, for an active extension, the flexion control valve 24 is closed and the extension control valve 25 is opened; in the case of an active flexion, the extension control valve 25 is closed and the flexion control valve 24 is opened.

Figure 3:
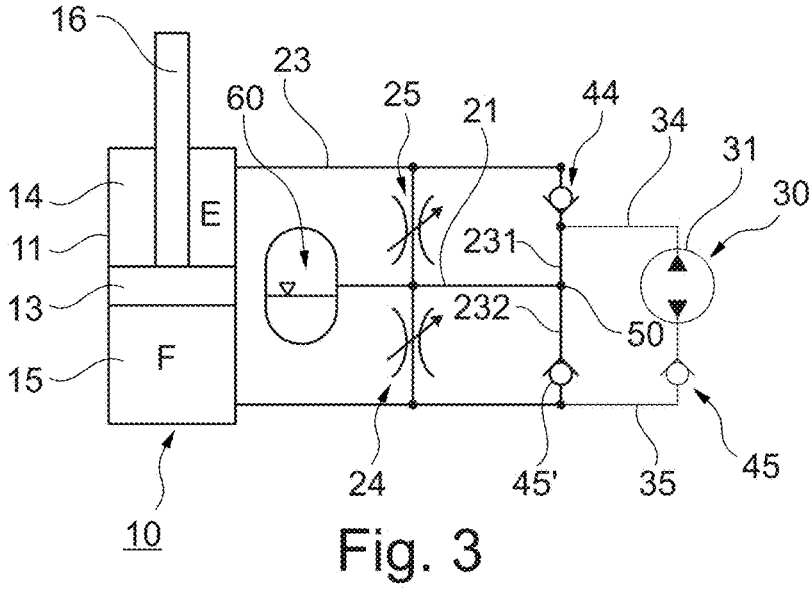
FIG. 3 shows a hydraulic circuit diagram for an active operating mode in one direction of movement.

If only support in the extension direction is desired in one embodiment, that is to say if the pump 30 is operated in only one direction in an active operating mode, a possible hydraulic circuit diagram for this is shown in FIG. 3. The pump 30 sucks in hydraulic fluid from the extension chamber 14 from a suction-side connection line 23 through the extension control valve 25; the flexion control valve 24 is advantageously closed. Through the central line 21, the hydraulic fluid is conveyed from the connection 50 through the supply line 231 and suction-side connection line 34 to the inlet 31 of the pump 31. If the pump pressure reaches and exceeds the pressure that is applied by the hydraulic fluid from the flexion chamber 15 against the check valve 45, the passive check valve 45 opens and hydraulic fluid is conveyed through the pressure-side connection line 35 into the flexion chamber 15. A backflow into the central line 21 is prevented by the check valve 45', which is arranged parallel to the check valve 45 in the pressure-side connection line 35 of the pump 30, and no hydraulic fluid can reach the low-pressure side or the central line 21 or the compensation container 60, such that when the pressure builds up accordingly, the piston 13 is moved upward and the piston rod 16 is extended out from the housing 11 in order to effect or support an extension movement. In addition to the hydraulic fluid from the extension chamber 14, hydraulic fluid is sucked in from the compensation volume 60 and conveyed in order to compensate for the volume difference through the piston rod 16. If the hydraulic actuator 100 is operated passively, the pump 30 is not driven and the extension movement or flexion movement is influenced by a variable cross section of flow through the adjustable control valves 24, 25. In the case of an extension, the fluid then no longer flows through the pump 30, but through the check valve 45' connected in parallel and the supply line 232 from the central line 21. Conversely, during flexion, the hydraulic fluid flows from the extension chamber 14 through the flexion control valve 24 and the check valve 44 into the flexion chamber 15 and parallel thereto into the compensation volume 60.

Figure 4:
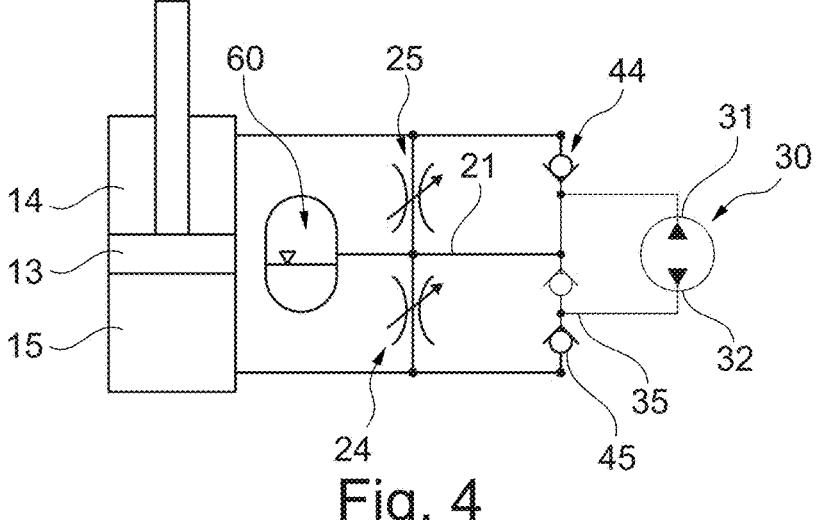
FIG. 4 shows a variant of FIG. 3.

A variant of the circuitry is shown in FIG. 4, in which likewise only an active support of an extension movement is provided. The pressure-side connection line 35, which leads from the outlet 32 of the pump 30 to the flexion chamber 15, opens out between two check valves 45, 45' oriented in the same direction. One check valve 45' blocks the flow from the pressure-side connection line 35 back to the central line 21; the second check valve 45 only opens when there is a sufficiently large pressure difference between the pressure-side connection line 35 and the return line to the extension chamber 14. Here too, in active operation, the flexion control valve 24 is advantageously closed, the extension control valve 25 is opened, such that pressurized fluid can flow from the flexion chamber 15 and the compensation volume 60 through the central line 21 to the inlet 31. During a passive extension movement, the hydraulic fluid does not flow through the inlet 31, but through the two check valves 45, 45', which are positioned on the low-pressure side during passive operation and allow a backflow into the extension chamber 14. If appropriate, the flexion control valve 24 can enable a throughflow.

The hydraulic circuit diagram of FIGS. 3 and 4 is configured for active support of an extension movement; in the case of flexion support alone, the connection of the pump 30 to the connection lines 34, 35 and the arrangement of the check valves would have to be carried out in a mirror-inverted manner on the other side of the central line 21.

Figure 5:
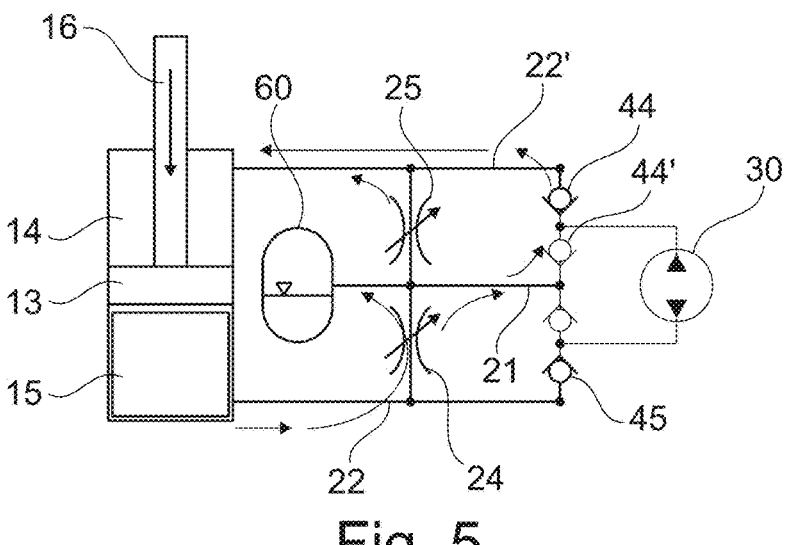
FIGS. 5 to 8 show flow profiles for active and passive operating modes in a circuit according to FIG. 2.
Figure 6:
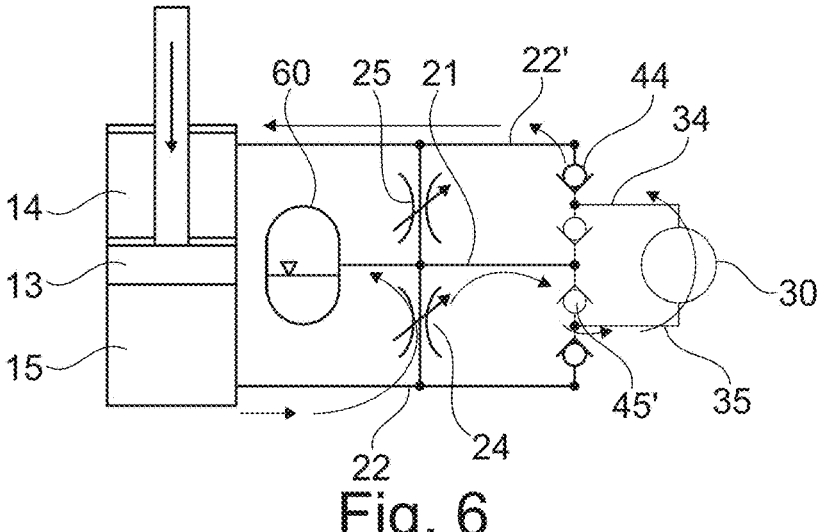
Figure 7:
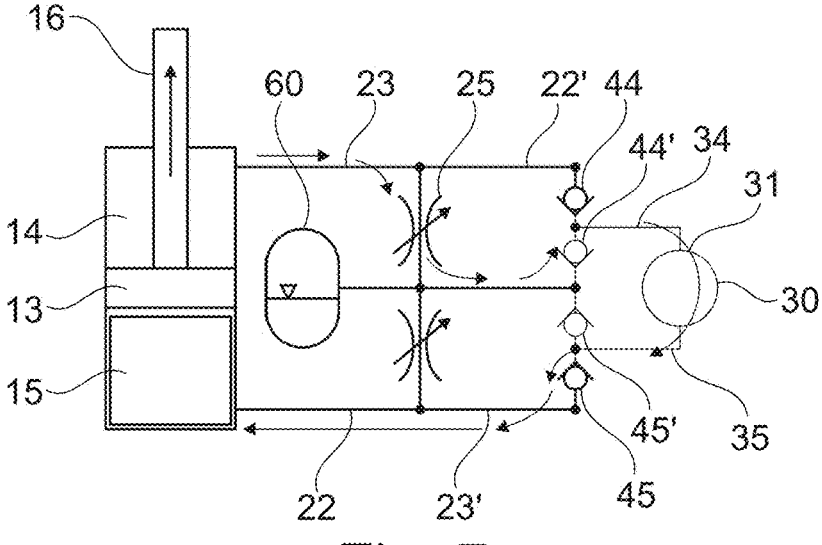
Figure 8:
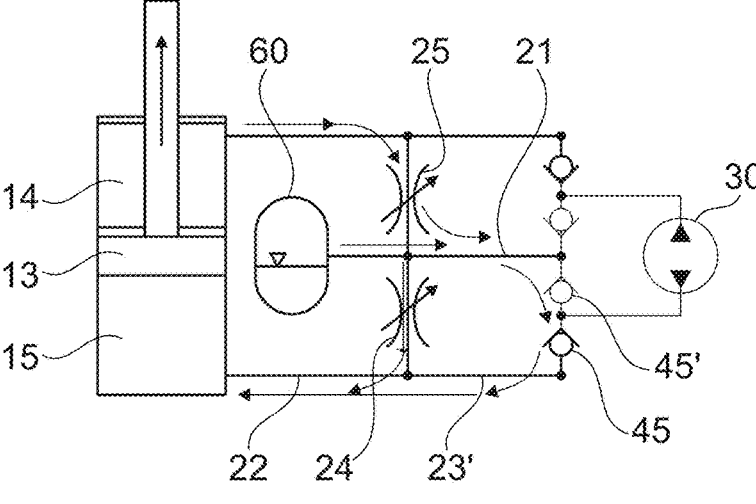

FIGS. 5 to 8 show switching states and flow paths in different operating modes. FIG. 5 shows a switching state for passive flexion, FIG. 6 shows a switching state for active flexion with a driven pump 30, FIG. 7 shows one for active extension and FIG. 8 shows one for passive extension. The circuitry corresponds to the circuitry in FIG. 2; for the sake of clarity, not all reference signs are indicated. In the case of a purely passive flexion, as is shown in FIG. 5, the piston 13 is moved downward with the piston rod 16, as is indicated by the arrow. As a result, the hydraulic fluid in the flexion chamber 15 is pressurized and flows out of the connection line 22 through the flexion control valve 24. A fluidic connection to the pump 30 is blocked by the check valve 45. The extension control valve 25 can be fully or partially opened. The hydraulic fluid flows out of the extension chamber partially into the compensation volume 60 and through the central line 21 and the upper pair of check valves 44, 44' into the extension chamber 14. Pressurized fluid from the extension chamber 15 is not conveyed to an inlet of the pump 30.

By contrast, if active support is desired, the extension control valve 25 is preferably closed and the flexion control valve 24 is opened. Hydraulic fluid is sucked in from extension chamber 14 and is therefore located in a low-pressure region. The fluid is sucked in through a suction-side connection line 35 through the central line 21 and the check valve 42'. A pressure increase takes place in the pump 30. The pressurized fluid is pumped through a pressure-side connection line 34 and a check valve 45, which blocks a backflow to the pump 30, and through a return line 22 to the flexion chamber 15. The piston 13 is pressed down, the piston rod 16 is retracted and a flexion is actively effected or supported. A partial volume flow flows out of the extension chamber 14 into the compensation volume 60.

In the case of an active extension, as is shown in FIG. 7, fluid flows out of the flexion chamber 15 through a suction-side connection line 23 through an opened extension control valve 25. Additionally required hydraulic fluid flows out of the compensation volume 60 into the central line 21 and from there through the check valve 44' to the inlet 31 of the pump 30. A second check valve 44 in the same direction blocks a direct inflow from the extension chamber 14 to a pump inlet 31. Hydraulic fluid flows from the driven pump 30 through a pressure-side connection line 35 through a check valve 45 through the return line 23', and the line functioning as connection line 22 in the case of a reverse movement, into the flexion chamber 15 and causes the piston rod 16 to move out, hence causing an extension movement.

In the passive circuit according to FIG. 8, the pump 30 remains deactivated, hydraulic fluid flows from the extension chamber 14, the extension control valve 25, the compensation volume 60 through the check valve pair 45, 45' and, if necessary, through an opened or partially opened flexion control valve 24 into the flexion chamber 15.

Figure 9:
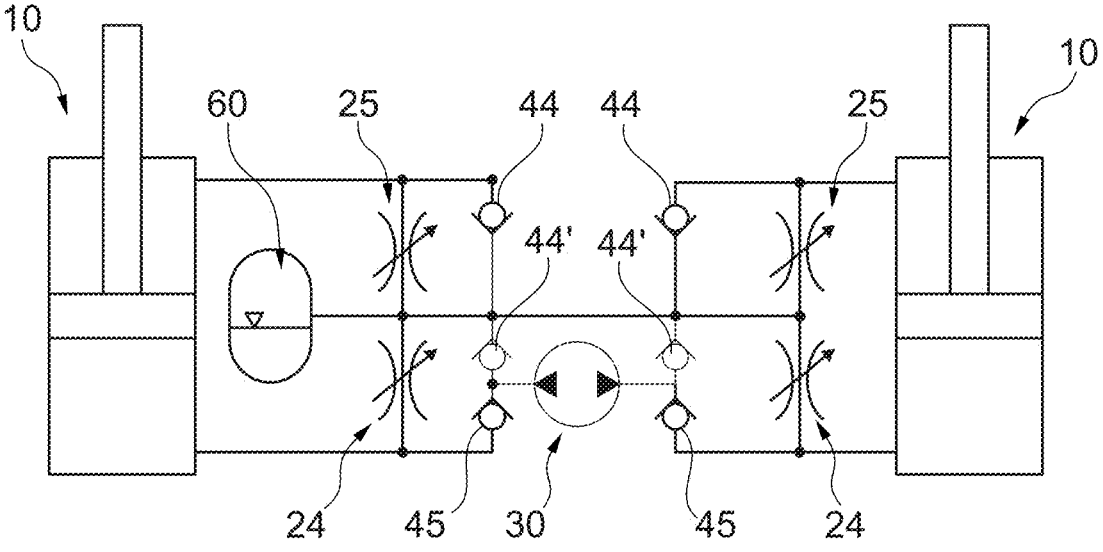
FIG. 9 shows a variant of a hydraulic actuator with two control elements.

FIG. 9 shows a further variant of the hydraulic actuator 100 in which two control elements 10 are coupled to each other. The basic set-up of the circuitry corresponds substantially to the circuitry shown in FIG. 2. Therefore, not all reference signs are indicated in FIG. 9. In a departure from FIG. 2, the motor-driven pump 30 is wired in such a way that both control elements 10 can be driven in at least one working direction or movement direction. If one control element 10 is arranged, for example, on an artificial knee joint and the other control element 10 is arranged on an artificial ankle joint, for example a plantar flexion and a knee extension can be brought about simultaneously by the pump 30. As an alternative to this, the circuitry can be set up in such a way that a knee flexion and a dorsiflexion or another combination of the respective flexion movement or extension movement takes place. In the embodiment according to FIG. 9 too, the connection lines to an inlet or outlet of the pump 30 open out between two identically directed check valves 44', 45. From there, pumped hydraulic fluid is conveyed via the return lines or connection lines to the respective chambers of the control elements 10. There is only one common compensation volume 60 present, which is connected to the central line. Both control elements 10 have flexion control valves 24 and extension control valves 25, via which it is possible to set different resistances of the respective control elements 10 in a passive operation or to achieve different adjustment paths for the respective control elements 10 by changing the flow resistances. With two control elements 10, it is also possible to decouple the pump 30 from the high-pressure side during active or passive operation and to only supply hydraulic fluid from the low-pressure region to the pump 30. This is made possible by the illustrated circuitry and arrangement of the check valves 44, 44', 45 and the arrangement of the control valves 24, 25 parallel thereto.

The invention claimed is:

1. A hydraulic actuator for orthoses or prostheses, comprising a control element with a housing in which a cylinder is arranged, in which a piston is mounted movably and divides the cylinder into a flexion chamber and an extension chamber, wherein a fluidic connection is arranged between the flexion chamber and the extension chamber, a control valve is arranged in the fluidic connection for influencing an extension movement and a flexion movement respectively, wherein a motor-driven pump is arranged in the fluidic connection, wherein hydraulic fluid is conveyed from a chamber selected from the flexion chamber and the extension chamber to the motor-driven pump through the control valve in a suction-side connection line, and two pressure-side check valves arranged in a pressure-side connection line from the motor-driven pump to an unselected chamber of the flexion chamber and the extension chamber and blocks a backflow of a pumped medium from this chamber to the motor-driven pump counter to a delivery direction of the motor-driven pump, wherein the pressure-side connection line, with which the motor-driven pump is connected to the fluidic connection, opens out between the two pressure-side check valves which act in a same direction and are arranged in series.

2. The hydraulic actuator as claimed in claim 1, wherein only one check valve is arranged between the motor-driven pump and the chamber pressurized by the motor-driven pump.

3. The hydraulic actuator as claimed in claim 1, wherein a check valve blocks a connection between the pressure-side connection line and a suction-side connection line.

4. The hydraulic actuator as claimed in claim 1, wherein a central line is formed in the fluidic connection, into which the central line, the suction-side connection line from the flexion chamber and the extension chamber open, and from which supply lines lead to at least one suction-side inlet to the motor-driven pump.

5. The hydraulic actuator as claimed in claim 4, wherein a control valve is arranged in the suction-side connection line.

6. The hydraulic actuator as claimed in claim 1, wherein the motor-driven pump has two pressure connections which are each connected to the fluidic connection via a respective pressure-side connection line, wherein both pressure-side connection lines open out between two check valves which are designed as pairs of check valves and which act in the same direction and are arranged in series, wherein the pairs of check valves have oppositely directed flow directions.

7. The hydraulic actuator as claimed in claim 4 wherein the central line leads to return lines to the extension chamber and flexion chamber, and at least one check valve is arranged in the return lines, wherein the check valve prevents a backflow into the central line.

8. The hydraulic actuator as claimed in claim 1, wherein the pressure-side connection line leads to a return line to the extension chamber or flexion chamber.

9. The hydraulic actuator as claimed in claim 1, wherein a compensation volume is connected to the fluidic connection.

10. The hydraulic actuator as claimed in claim 1, wherein the piston is coupled to a piston rod which protrudes from the housing and which is mounted so as to be linearly movable.

11. The hydraulic actuator as claimed in claim 1, wherein the motor-driven pump is designed or connected so as to be able to be operate to fill both the extension chamber and the flexion chamber.

12. The hydraulic actuator as claimed in claim 1, wherein the two pressure-side check valves are designed as passive valves.

13. The hydraulic actuator as claimed in claim 1, wherein the control valves are electronically controlled.

14. The hydraulic actuator as claimed in claim 1, wherein a plurality of control elements are fluidically coupled to the motor-driven pump.

15. An orthopedic device with a hydraulic actuator as claimed in claim 1.

16. The orthopedic device as claimed in claim 15, wherein the hydraulic actuator is designed to be able to be operated as an active actuator or as a passive actuator.

17. The orthopedic device as claimed in claim 15, wherein the control element is arranged between a joint device with an upper part and with a lower part attached to the latter in an articulated manner.

18. The orthopedic device as claimed in claim 15 wherein two control elements connected to a common pump are arranged on different joint devices of the orthopedic device.

19. A hydraulic actuator for orthoses or prostheses comprising:

a control element with a housing in which a cylinder is arranged, in which a piston is mounted movably and divides the cylinder into a flexion chamber and an extension chamber;

wherein a fluidic connection is arranged between the flexion chamber and the extension chamber, a control valve is arranged in the fluidic connection for influencing an extension movement and a flexion movement respectively, wherein a motor-driven pump is arranged in the fluidic connection, wherein hydraulic fluid is conveyed from one chamber to the motor-driven pump through the control valve in a suction-side connection line, and wherein a check valve is arranged in a pressure-side connection line from the motor-driven pump to the other chamber and blocks a backflow of a pumped medium from this chamber to the motor-driven pump counter to a delivery direction of the motor-driven pump;

wherein the pressure-side connection line opens out between two check valves which act in the same direction and are arranged in series, and wherein a check valve blocks a connection between the pressure-side connection line and a suction-side connection line.

* * * * *